United States Patent
Stokowski

(10) Patent No.: US 7,738,092 B1
(45) Date of Patent: Jun. 15, 2010

(54) SYSTEM AND METHOD FOR REDUCING SPECKLE NOISE IN DIE-TO-DIE INSPECTION SYSTEMS

(75) Inventor: Stan Stokowski, Danville, CA (US)

(73) Assignee: KLA-Tencor Corporation, San Jose, CA (US)

( * ) Notice: Subject to any disclaimer, the term of this patent is extended or adjusted under 35 U.S.C. 154(b) by 334 days.

(21) Appl. No.: 11/970,618

(22) Filed: Jan. 8, 2008

(51) Int. Cl.
*G01N 21/00* (2006.01)

(52) U.S. Cl. .................. 356/237.5; 356/237.2

(58) Field of Classification Search .... 356/237.1–237.5
See application file for complete search history.

(56) References Cited

U.S. PATENT DOCUMENTS

| | | | |
|---|---|---|---|
| 6,081,381 A | 6/2000 | Shalapenok et al. | |
| 6,747,781 B2 | 6/2004 | Trisnadi | |
| 7,271,962 B2 | 9/2007 | Kasazumi et al. | |
| 7,304,731 B2 * | 12/2007 | Hill | 356/237.2 |
| 7,326,623 B2 * | 2/2008 | Hongo et al. | 438/308 |
| 7,463,350 B2 * | 12/2008 | Nishiyama et al. | 356/237.4 |
| 7,630,069 B2 * | 12/2009 | Naftali et al. | 356/237.2 |
| 2005/0128473 A1 | 6/2005 | Karpol et al. | |
| 2006/0066870 A1 | 3/2006 | Korngut et al. | |
| 2006/0152810 A1 | 7/2006 | Kvamme | |
| 2007/0008519 A1 | 1/2007 | Naftali et al. | |
| 2007/0242253 A1 | 10/2007 | Visser et al. | |

\* cited by examiner

*Primary Examiner*—Michael P Stafira
(74) *Attorney, Agent, or Firm*—Kevin L. Daffer; Daffer McDaniel, LLP

(57) ABSTRACT

Systems and methods are provided herein for eliminating speckle noise in die-to-die inspection systems. In one embodiment, an illumination system in accordance with the present invention may include a coherent light source, a diffuser, a first detector, a second detector and a controller. The diffuser may be coupled within an illumination path between the coherent light source and the specimen. In one embodiment, the diffuser may be a rotational diffuser having a variable rotational rate. The first detector may be coupled for detecting a desired position on the specimen. The second detector may be coupled for detecting a rotational position of the diffuser when the desired position on the specimen is detected. The controller may be coupled to: (i) the first and second detectors for determining a difference between the rotational position of the diffuser and the desired position on the specimen, and (ii) the diffuser for adjusting the rotational rate of the diffuser to eliminate the difference.

20 Claims, 4 Drawing Sheets

SYSTEM AND METHOD FOR REDUCING SPECKLE NOISE IN DIE-TO-DIE INSPECTION SYSTEMS

BACKGROUND OF THE INVENTION

1. Field of the Invention

This invention relates to inspection systems and, more particularly, to inspection systems and methods for reducing speckle noise in images.

2. Description of the Related Art

The following descriptions and examples are given as background only.

Fabricating semiconductor devices such as logic and memory devices typically includes processing a substrate using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during the manufacturing process to detect defects on wafers, promoting higher yield in the manufacturing process, and thus, higher profits. Inspection has always played an important role in the fabrication of semiconductor devices. However, the performance requirements of inspection systems continues to increase, as the dimensions of the semiconductor devices decrease. In comparison to previous systems, today's inspection systems require significantly higher resolution and sensitivity for detecting the small sized defects, which occur on advanced semiconductor wafers.

One way to increase the resolution of an optical inspection system is to decrease the wavelength at which the system can operate. For instance, resolution is defined as: Resolution=$\lambda$/n(NA), where $\lambda$ is the wavelength, n is the index of refraction, and NA is the numerical aperture of the optical system at the object. Therefore, resolution increases as wavelength decreases. In some systems, however, steps taken to increase resolution have an adverse affect on the sensitivity of the system.

For example, there are generally two types of light sources available for use in an optical inspection system. In some cases, an incoherent light source (such as, e.g., an arc lamp, a tungsten incandescent lamp, a deuterium lamp, and a light-emitting diode) may be used to illuminate the semiconductor wafer of specimen. However, most incoherent light sources are incapable of producing light with sufficient brightness as the wavelength of the inspection system is decreased (e.g., to increase resolution). The relative brightness of the light source affects defect sensitivity by affecting the signal-to-noise ratio of the output signals generated by the inspection system. If the brightness is too low, the signal-to-noise ratio may be too low for accurate defect detection. In some cases, the inspection throughput may be reduced to allow enough light to be collected. Obviously, reduced throughput is highly undesirable for inspection.

Therefore, a laser light source is often used to generate brighter light at shorter wavelengths. However, laser light sources produce coherent light, which is undesirable for inspection for many reasons. For example, coherent light tends to introduce speckle and/or ringing into the inspection images generated by the image detector. Speckle decreases the sensitivity of the inspection system by decreasing the signal-to-noise ratio of the output signals generated by the inspection system. Ringing introduces artifacts into the inspection images, which reduce sensitivity and make it difficult to detect defects. Many illumination systems have been designed to mitigate the affects of speckle and/or ringing.

In some cases, speckle and/or ringing may be improved by reducing the spatial coherence of the laser light used to illuminate the specimen. One technique for providing partially incoherent laser light involves the use of a rotating diffuser. The diffuser is arranged within the path of the incident laser beam and rotated to introduce random phase variations into the beam.

As the diffuser rotates, multiple images of the specimen are collected from independent views or perspectives by an image detector (e.g., a CCD or TDI detector). The multiple images are averaged over the integration time of the image detector to reduce speckle and ringing. For example, the mask inspector 5xx provided by KLA-Tencor Corp. of San Jose, Calif. includes a diffuser, which may be configured for averaging approximately 250,000 images over the integration time of the image detector (e.g., about 0.5-1.0 msec). Since the noise reduction factor is the square root of the number of images averaged, the diffuser may provide a noise reduction factor of about 500 times.

In some cases, further noise reduction may be needed as device dimensions continue to shrink to smaller and smaller sizes. One obvious way to reduce noise is to increase the number of images averaged. However, in order to do so, one would have to either: (a) increase the integration time of the detector, or (b) increase the rotational rate of the diffuser. Increasing the integration time of the detector is usually undesirable because it reduces the throughput of the inspection system. However, increasing the rotational rate of the detector may not be desirable, either. For example, the diffuser included within the mask inspector 5xx currently rotates at about 20,000 rpm. Increasing the rotational rate to higher rotational speeds may lead to stress, vibrations and potential damage.

Therefore, a need exists for an improved inspection system and method for reducing speckle in images obtained using coherent illumination. Preferably, the system and method would minimize speckle and improve defect sensitivity, while maintaining inspection throughput and avoiding undue stress on rotational system components.

SUMMARY OF THE INVENTION

The following description of various embodiments of illumination systems, inspection systems and methods is not to be construed in any way as limiting the subject matter of the appended claims.

According to one embodiment, a system is provided herein for providing illumination to a specimen under inspection. Among other components, the illumination system may include a coherent light source, a diffuser, a reflective optical component, a lens, a stage, an auto-focus unit, a first detector, a second detector and a controller. The diffuser is arranged within the illumination path between the coherent light source and the specimen for reducing the coherency of the light generated by the coherent light source. In one embodiment, the diffuser may be a rotational diffuser comprising a variable rotational rate. The reflective optical component is arranged within the illumination path for directing light exiting the diffuser onto a surface of the specimen. The lens is arranged within the illumination path for focusing the light, which is directed onto the surface of the specimen. The autofocus unit is coupled within the illumination path for adjusting a position of the lens to maintain the surface of the specimen within a focus region of the lens.

The specimen is mounted on a stage. Movement of the stage causes the focused light to be scanned across two adjacent die on the specimen. The first detector is coupled for detecting a desired position on the specimen as the light is scanned across the two adjacent die. The second detector is coupled for detecting a rotational position of the diffuser when the desired position on the specimen is detected. In one embodiment, the stage and the diffuser may each have a reference mark, which enables the first and second detectors to detect the desired position and the rotational position, respectively.

The controller is coupled to the first and second detectors for determining a difference between the rotational position of the diffuser and the desired position on the specimen. In some embodiments, the controller may be coupled to the diffuser for adjusting the rotational rate of the diffuser to eliminate the difference. In particular, the controller may adjust the rotational rate of the diffuser, so that an integral number of rotational periods occurs between identical features on the two adjacent die. In some embodiments, the controller may also be coupled to the reflective optical component for adjusting an angle at which the light is directed onto the surface of the specimen. Since the reflective optical component is arranged in the Fourier transform plane of the lens, a the angular adjustment results in a linear shift in position of the light directed to the surface.

According to another embodiment, a system is provided herein for inspecting a specimen. The system may generally include an illumination subsystem, a detection subsystem and a control subsystem. Among other components, the illumination subsystem may include a rotating diffuser arranged within an illumination path between a coherent light source and the specimen; a reflective optical component arranged within the illumination path for directing light exiting the diffuser across a surface of the specimen; a lens arranged within the illumination path for focusing the light, which is directed onto the surface of the specimen; and a stage upon which the specimen is mounted, wherein movement of the stage causes the focused light to be scanned across two adjacent die on the specimen.

In one embodiment, the detection subsystem may include a first detector, a second detector and a third detector. The first detector may be coupled for detecting a desired position on the specimen. The second detector may be coupled for detecting a rotational position of the diffuser when the desired position is detected. The third detector may be coupled for receiving light propagating from the surface of the specimen and for generating images of the two adjacent die in response thereto. The images obtained using the third detector may used be for detecting defects on the specimen.

In one embodiment, the control subsystem may be coupled to the first and second detectors for determining a difference between the rotational position of the diffuser and the desired position on the specimen. The control subsystem may also be coupled to the diffuser and the reflective optical component. For example, the control subsystem may be coupled to the diffuser for adjusting a rotational rate of the diffuser to eliminate the difference. In addition, the control subsystem may be coupled to the reflective optical component for adjusting an angle at which the light is directed onto the surface of the specimen.

As such, the control subsystem may cause substantially identical speckle noise patterns to be produced in the images of the two adjacent die by: (i) adjusting the rotational rate of the diffuser, so that an integral number of rotational periods occurs between identical features on the two adjacent die; and (ii) adjusting the angle at which the light is directed onto the surface of the specimen, such that the difference between the rotational position of the diffuser and the desired position on the specimen is substantially zero. In one embodiment, a substantially zero difference may be equivalent to about one image pixel, as measured by the first and second detectors.

According to yet another embodiment, a method is provided herein for inspecting a specimen comprising a plurality of die having substantially identical features formed thereon. In one embodiment, the method may include illuminating a diffuser with coherent light; scanning light exiting the diffuser across a surface of the specimen; detecting light propagating from the surface of the specimen as light from the diffuser is scanned across two adjacent die to obtain images of the two adjacent die; controlling a rotational rate of the diffuser, so that an integral number of rotational periods occurs between identical features on the two adjacent die; and subtracting the images obtained from the two adjacent die to detect defects on the specimen.

In one embodiment, the step of controlling may include: (i) counting the number of times the coherent light passes through a reference mark on the diffuser as the light from the diffuser is scanned between the identical features on the two adjacent die, and (ii) adjusting the rotational rate of the diffuser. In some cases, the rotational rate may be increased if the number of times is substantially less than the integral number. In other cases, the rotational rate may be decreased if the number of times is substantially greater than the integral number. If the number of times is not equivalent to the integral number after the steps of counting and adjusting, the method may include an additional step of adjusting an angle at which the light is directed onto the surface of the specimen. As noted above, the angle can be adjusted in one or more directions to produce a linear shift in position of the light directed to the surface of the specimen.

In a preferred embodiment, the steps of adjusting the rotational rate and adjusting the angle enable substantially identical noise patterns to be generated in each of the images by aligning a position of the diffuser with a desired position on the specimen. When the images are subtracted, the steps of adjusting the rotational rate and adjusting the angle reduce noise in the images obtained from the two adjacent die by removing the substantially identical noise patterns produced in each of the images.

BRIEF DESCRIPTION OF THE DRAWINGS

Other objects and advantages of the invention will become apparent upon reading the following detailed description and upon reference to the accompanying drawings in which.

Figure 1:
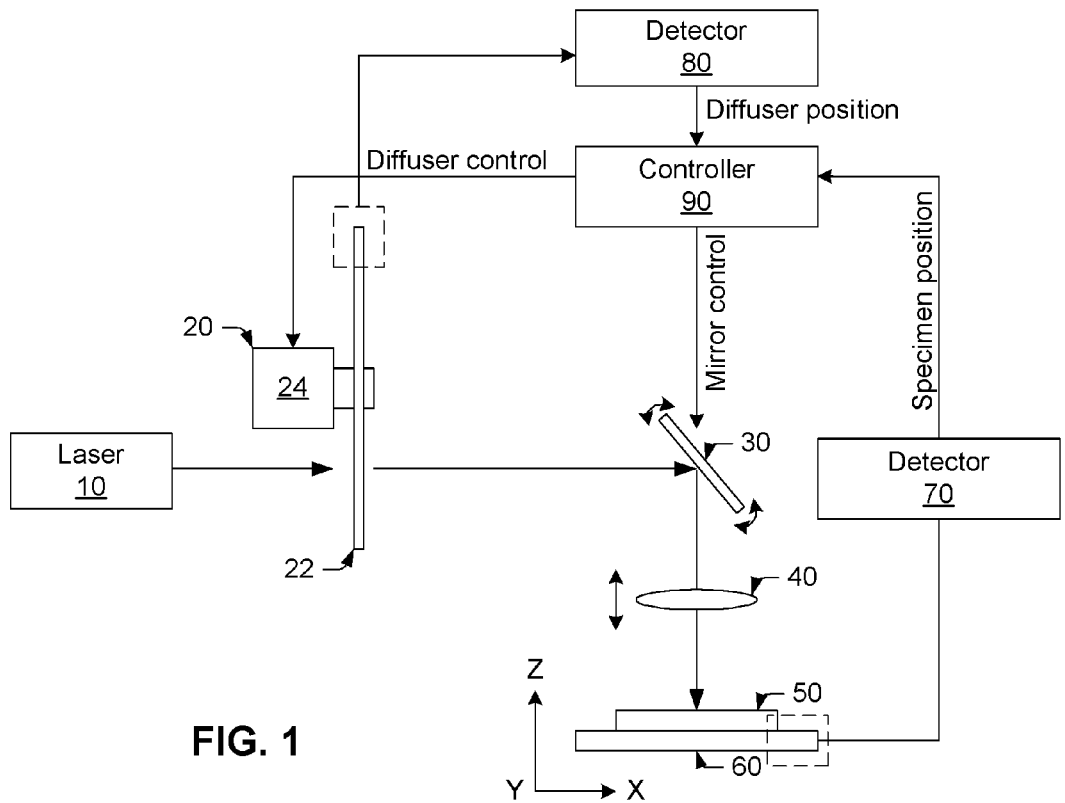
FIG. 1 is a block diagram of an illumination system, according to one embodiment of the invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

As used herein, the term "specimen" refers to a reticle or a wafer. The terms "reticle" and "mask" are used interchangeably herein. A reticle generally includes a transparent substrate such as glass, borosilicate glass, and fused silica having opaque regions formed thereon in a pattern. In some cases, the opaque regions may be replaced by regions etched into the transparent substrate. In some cases, the pattern may be replicated one or more times, such that a plurality of "dice" are formed on the substrate. Many different types of reticles are known in the art, and the term reticle as used herein is intended to encompass all types of reticles.

As used herein, the term "wafer" generally refers to substrates formed of a semiconductor or non-semiconductor material. Examples of a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term "wafer" as used herein is intended to encompass a wafer including all types of such layers. One or more layers formed on the wafer may be patterned or unpatterned. For example, a wafer may include a plurality of "dice," each having a repeatable pattern of features. Formation and processing of such layers of material may ultimately result in completed devices. Many different types of devices may be formed on a wafer, and the term "wafer" as used herein is intended to encompass a wafer on which any type of device known in the art is being fabricated.

Many different types of inspection tools have been developed for the inspection of specimens, including optical and E-beam systems. As used herein, the term "inspection system" refers to an optical inspection system, and more specifically, a bright-field (BF) optical inspection tool. Bright-field inspection systems direct light to a specimen at a particular angle (or a range of angles) and measure the amount of light reflected from or transmitted through the surface of the specimen at a similar angle (or angles). The measured light is typically used by the bright-field inspection system to detect a pattern on the specimen.

Some optical inspection systems may be configured in a reflective or transmissive mode for collecting light from the specimen. In reflective mode, the illumination and the collection light pass through a single imaging objective. On the other hand, a condenser lens is used in transmissive mode to focus the illumination light onto the object, whereas light transmitted through the object is collected by an imaging objective. The inspection system described below may be configured for operating in either reflective or transmissive mode. However, one skilled in the art would understand how the inspection system shown herein may be modified to operate in only one mode.

There are several methods, which may be used for inspecting specimens. These methods generally include: "Die-to-Die" inspection, in which a die is compared to a purportedly identical die on the same specimen; "Die-to-Database" inspection, in which data pertaining to a given die is compared to information in a database; and "Die-to-Reference Die" inspection, in which a single die is chosen as a reference for inspecting the specimen. There is also a design rule based inspection method, in which a die under inspection must fulfill certain line width and spacing requirements and include feature shapes that fit predefined shapes. As used herein, the term "inspection" preferably refers to Die-to-Die inspection of a specimen comprising a plurality of substantially identical die.

In Die-to-Die inspection, images of two purportedly identical die are aligned and then subtracted to remove the repeatable pattern features included within each die. In theory, defects should be readily detectable from the difference image once the repeatable pattern features are removed. However, defects in the difference image are often obscured by other artifacts. For example, many inspection systems attempt to increase image resolution by using laser light sources, which are capable of producing brighter light at shorter wavelengths. Unfortunately, laser light sources produce coherent light, which tends to introduce speckle and/or ringing into the inspection images generated by the image detector. Speckle decreases the sensitivity of the inspection system by decreasing the signal-to-noise ratio of the output signals generated by the inspection system. Ringing introduces artifacts into the inspection images, which reduce sensitivity and make it difficult to detect defects.

In some cases, speckle may be reduced by inserting a rotating diffuser within the illumination system. The rotating diffuser reduces the coherence of the illumination light by scattering the light to introduce random phase variations into the laser beam. As the diffuser rotates, multiple images of the specimen are collected from independent views or perspectives by the image detector. Speckle is reduced by averaging the images obtained over the integration time of the image detector. In some cases, speckle can be reduced by a significant amount (e.g., up to about 500 times) by averaging a large number of images (e.g., about 250,000 images) over the integration time of the detector. However, the amount of noise reduction may be insufficient in newer technologies with smaller device dimensions (e.g., about 45 nm and below).

The present invention provides an improved inspection system and method for reducing speckle in images obtained using coherent illumination. As set forth in more detail below, the improved inspection system and method minimizes speckle and improves defect sensitivity, while maintaining inspection throughput and avoiding undue stress on rotational system components. The improved inspection system and method described herein achieves these advantages, in part, by correlating speckle noise with diffuser position.

For example, the inspection system and method described herein may use a transmissive type diffuser, such as a ground glass diffuser or programmed diffuser. A ground glass diffuser randomly scatters the illumination light over an angular distribution. Unlike typical diffusers, which scatter light in a Gaussian manner, a programmed or printed diffuser may be configured to generate pseudo-random diffraction of light incident thereon. Regardless of the particular type used, the diffuser will produce a speckle pattern within the illumination light, which is directly related to the microscopic details of the diffuser surface providing the scattering. This means that a substantially identical speckle pattern is produced every time the diffuser makes one full rotation. Speckle noise is eliminated in the die-to-die inspection system and method described herein by ensuring that the diffuser rotates an integer number of rotational periods between identical features on two adjacent die. This ensures that the pattern and the speckle illumination field will be the same in the images obtained of the two die, thus enabling both the pattern and the speckle noise to be eliminated when the difference image is taken.

Eliminating speckle noise enables defects to be more easily detected by increasing the signal-to-noise (S/N) ratio of the die-to-die inspection system. However, speckle noise is eliminated only if the speckle illumination field is exactly the same between the identical features on the two adjacent die. As set forth below, a substantially identical speckle illumination field may be achieved by adjusting the rotational rate of the diffuser, so that an integral number of rotational periods occurs between the identical features. In some cases, additional means may be used to ensure that the speckle illumination field is the same in all three directions (i.e., x, y and z).

Turning now to the drawings, it is noted that the figures are not drawn to scale. In particular, the scale of some of the elements of the figures may be greatly exaggerated to emphasize characteristics of those elements. It is also noted that the figures are not drawn to the same scale. Elements shown in more than one figure that may be similarly configured have been indicated using the same reference numerals.

FIG. 1 illustrates one embodiment of a system configured to provide illumination to a specimen under inspection. As used herein, the specimen under inspection may be a wafer (FIG. 2A) or a mask (FIG. 2B), which includes a plurality of die having substantially identical patterned features. The plurality of die are arranged in an array of closely packed die, such that each succeeding die is adjacent to the previous die in any given row or column. For example, the specimen shown in FIG. 2A (a wafer) includes a 7×9 array of adjacent die, whereas a 1×2 array of adjacent die is formed on the specimen shown in FIG. 2B (a mask). However, the specimen described herein is not limited to any particular size of array, and may generally include an M×N array of substantially identical die, where at least one of the dimensions (i.e., M or N) is greater than one.

The illumination system shown in FIG. 1 includes a light source 10 configured to illuminate diffuser 20 with coherent light. Light source 10 may include substantially any laser light source, examples of which include but are not limited to, continuous wave gas and solid state lasers, pulsed solid state lasers, excimer gas lasers, etc. The coherent light from light source 10 impinges upon rotating disk 22 of diffuser 20. In some cases, the rotational rate of disk 22 may be adjusted by modifying the power supplied to diffuser motor 24. In one embodiment, the rotational rate may be adjustable throughout a range comprising about 300 Hz to about 340 Hz. However, diffuser 20 is not limited to a particular range of rotational rates, and may be configured to operate over a substantially smaller or larger range in other embodiments of the invention. It is also worth mentioning that diffuser 20 is not necessarily limited to a rotational diffuser. In one alternative embodiment, a translational diffuser (not shown) may be used in place of the rotational diffuser shown in FIG. 1. However, because translational diffusers are typically limited to slower rates (e.g., up to about 50 Hz), they may not be applicable to all embodiments of the invention.

As shown in FIG. 1, reflective optical component 30 is arranged within the illumination path for directing light exiting the diffuser onto a surface of specimen 50. Lens 40 is arranged between optical component 30 and specimen 50 for focusing the light, which is directed onto the surface. Lens 40 may be a refractive lens, such as a spot lens, or any other suitable optical component known in the art. In some embodiments, lens 40 may represent a compound objective, which is used for focusing the illumination light onto the specimen in either reflective or transmissive mode (see, e.g., FIGS. 3-4). Therefore, although lens 40 is shown as a single optical component in FIG. 1, it is to be understood that lens 40 may include more than one optical component in other embodiments of the invention.

Component 30 may be any reflective optical component, which is capable of adjusting the angle at which the illumination light is directed to the surface of the specimen. Examples of such components include, but are not limited to, mirrors, transparent plates and acousto-optic deflectors that are tiltable in at least two directions (e.g., x and y directions) for changing the angle of the illumination light. As described in more detail below, reflective optical component 30 is positioned at the Fourier transform plane of lens 40 so that a change in illumination angle results in a linear shift (x or y) in the position of the illumination field presented to the specimen. In some embodiments, the illumination angle may be adjusted to ensure that the illumination fields presented to two adjacent die are exactly the same. In addition to the x and y adjustments provided by component 30, lens 40 may be translated in the z-direction to ensure that the surface of the specimen remains within a focus region of the imaging objective (see, e.g., FIGS. 3-4).

As shown in FIG. 1, specimen 50 is mounted on a stage 60 that moves in the x and y directions. Upon completing a scan in the x-direction, the stage is stepped in the y-direction and the next x-direction scan is taken. An imaging objective (not necessarily shown in FIG. 1) generates an optical image of the specimen as the illumination light is scanned across the surface of the specimen in the x and y directions. A detector (not shown in FIG. 1) converts the optical image into an electronic signal, which can be analyzed and displayed. In one embodiment, a time-delay integration (TDI) detector may be used to convert the optical images into electronic signals. A TDI detector operates by moving the photo-electrons in a given image pixel synchronously with the stage movement in the x-direction.

In order to effectively eliminate speckle, we need to ensure that the speckle illumination fields presented to two adjacent die are exactly the same. Since the speckle field is a function of all three dimensions (i.e., x, y and z), the speckle field must be accurately aligned to the same repeating patterns on the specimen in all three directions as the illumination light moves from one die to the next. This can be achieved, in one embodiment, by using several different methods of alignment.

First of all, the speckle illumination field can be adjusted in the x-direction by controlling the rotational rate of diffuser 20, so that an integral number of diffuser rotational periods occurs between identical features on two adjacent die. Since the plurality of die are supposedly the same, the identical features appearing on each die will be consistently spaced from one die to the next. The spacing between identical features is shown, e.g., as die-to-die distance, D, in FIGS. 2A-2B. If the diffuser rotates an integer (n) number of times over a given die-to-die distance (D), the time (T) needed for the diffuser to make one full rotation will be:

$$T = \frac{D}{nv} \qquad \text{EQ.1}$$

where v is the velocity of the stage (60) as it scans from one die to the next. Since the rotational rate (R) is inversely proportional to T, the rate may be expressed as:

$$R = \frac{1}{T} = \frac{nv}{D} \qquad \text{EQ.2}$$

Assume, e.g., that D=50 mm, v=25 mm/sec and T is approximately 3 ms. If this is the case, diffuser 20 will rotate approximately n=667 times between identical features on two adjacent die with a rotational rate (R) of about 333.5 Hz. As set forth below, the integer number of rotations (n) may be maintained from one die to the next by monitoring the rotational position of diffuser 20 relative to a desired position on specimen 50 and controlling the diffuser rotational rate (R) to eliminate any differences there between.

As shown in FIG. 1, a first detector 70 may be included within the illumination system for monitoring the position of the specimen. In one embodiment, detector 70 may be used to detect a desired position on the specimen by monitoring a reference point on the stage 60. In some cases, the reference point may be a fine scale, which is imprinted on the stage to monitor the stage position. In other cases, an interferometer may be used to monitor the position of the stage. Both techniques are well known in the art and will not be further discussed herein.

As shown in FIG. 1, a second detector 80 may be included within the illumination system for detecting the rotational position of diffuser 20 once the desired position on the specimen is detected. In one embodiment, detector 80 may detect the rotational position of the diffuser by monitoring a reference point on the rotational disk 22. In some embodiments, the reference point may be a fine scale, which is imprinted on the rotational disk to monitor the rotational position of the diffuser. However, this represents only one method for accomplishing the task; other methods known to those skilled in the art may also be used.

As the illumination light moves from one die to the next, the stage and diffuser positions detected by detectors 70 and 80 are supplied to controller 90. The controller compares the rotational position of the diffuser to the desired position on the specimen and determines if any differences exist. If differences do exist (i.e., if the rotational position of the diffuser is not aligned with the desired position on the specimen), the controller adjusts the rotational rate (R) of the diffuser to eliminate the difference. In some cases, the rotational rate may be adjusted by modifying the power supplied to the diffuser motor 24 as indicated above.

In one embodiment, the controller may compare the stage and diffuser positions in terms of number of pixels. The pixel size is typically determined by the detectors 70/80 chosen for detecting the positions of the specimen and the diffuser. In one example, detectors 70 and 80 may generate a pixel size (p) of about 72 nm (where p is measured at the specimen plane). If the die-to-die distance (D) between identical features is approximately 50 mm, the distance D may be approximately equal to D/p=50 mm/72 nm=694,444 pixels. (Note: if the ratio of D/p is not exactly an integer number of pixels, the ratio can be rounded to the nearest integer.) If, as noted in the example provided above, the diffuser makes n=667 rotations within the distance D, one full rotation of the diffuser should correspond to approximately 694,444/667 or 1041.14 pixels.

The stage position measurement from detector 70 tells the controller how fast the specimen is moving in pixels/second. In one embodiment, the controller may compare the stage position measurement to the diffuser position measurement once every 30 msec, or approximately once every 10 rotations. If the diffuser position is properly aligned to the desired position on the stage, the controller should detect 10×1041.14 pixels, or about 10,411.4 pixels of stage motion for every 10 rotations of the diffuser disk. If a smaller or larger number of pixels of stage motion is detected, the controller may issue a control signal ("diffuser control") to the diffuser to adjust the rotational rate and account for the difference. If, for example, detector 70 reports a stage position measurement of 10,411.8 pixels, instead of 10,411.4 pixels, the controller may determine that an x-direction alignment error of approximately −0.4 pixels exists between the rotational position of the diffuser and the desired position on the specimen. To compensate for such error, the controller may supply a control signal to diffuser 20 to increase the diffuser rotational rate by approximately 0.4/10,411.4=0.0038%.

In some cases, the speckle illumination field may be "tweaked" to ensure that the illumination fields presented to the two adjacent die are exactly the same. As noted above, the speckle illumination field may be adjusted slightly in the x and/or y directions by changing the angle at which the light is directed to the specimen. This is achieved in FIG. 1 by tilting reflective optical component 30 in the appropriate direction. Since component 30 is located in the Fourier transform plane of the focusing lens 40, a change in illumination angle results in a linear shift (x and/or y) in the position of the speckle illumination field. If, as noted above, detector 70 reports a −0.4 pixel error in the x-direction, reflective optical component 30 may be tiled in the x-direction to shift the illumination field by −0.4 pixels. Component 30 may also be adjusted in the y-direction if detector 70 reports a y-direction pixel error. For the z-direction, an auto-focus system (not shown in FIG. 1) may be used to keep the specimen within the focus region of the imaging objective by adjusting the position of lens 40 in the z-direction.

In some embodiments, controller 90 may compare the stage and diffuser position measurements at a rate consistent with the number of rotations averaged. If this number is 10, then a comparison can be made every 30 ms, as discussed above. However, the controller is not limited to averaging a particular number of rotations, and thus, may perform a comparison more or less frequently than discussed above. Increasing the comparison rate allows high frequency errors to be compensated, but with more noise, whereas decreasing the rate provides better noise averaging for lower frequency errors. The system may be configured, as needed, to provide an optimum rate.

Figure 3:
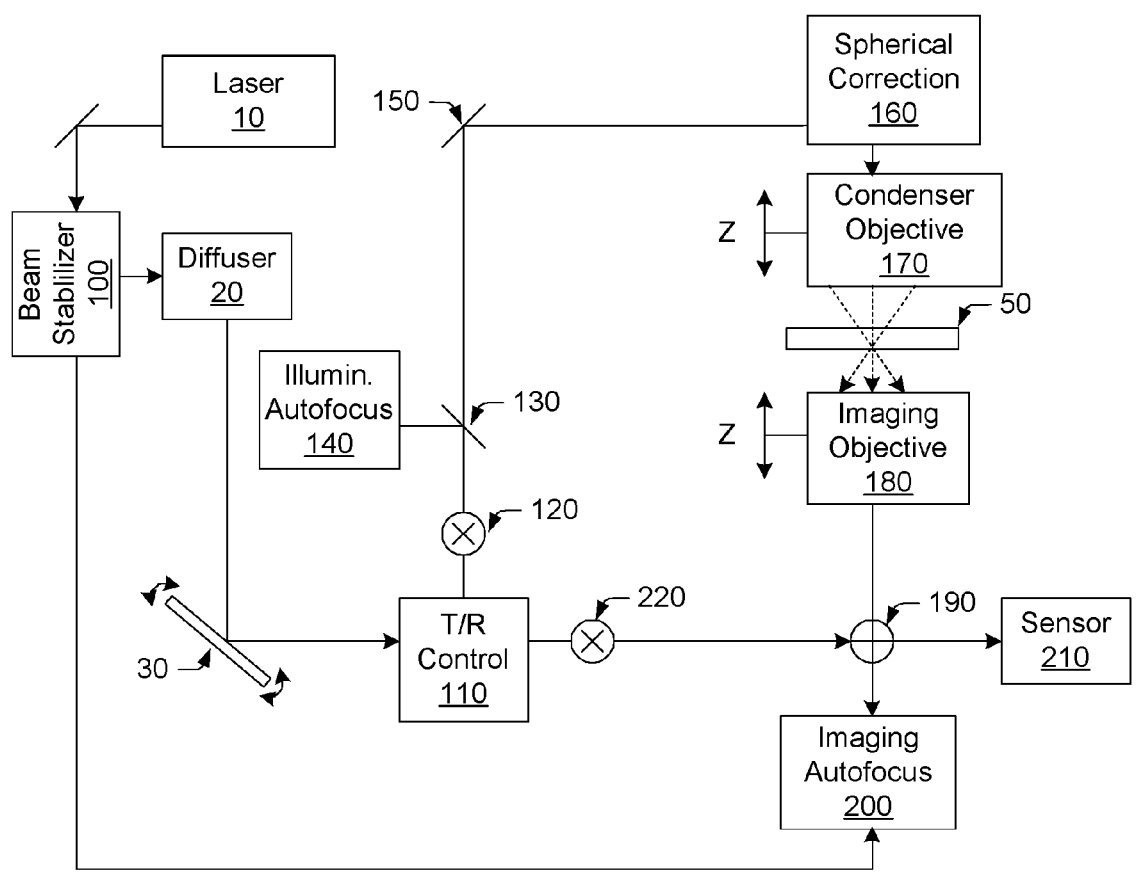
FIG. 3 is a block diagram of an inspection system, according to one embodiment of the invention.
Figure 4:
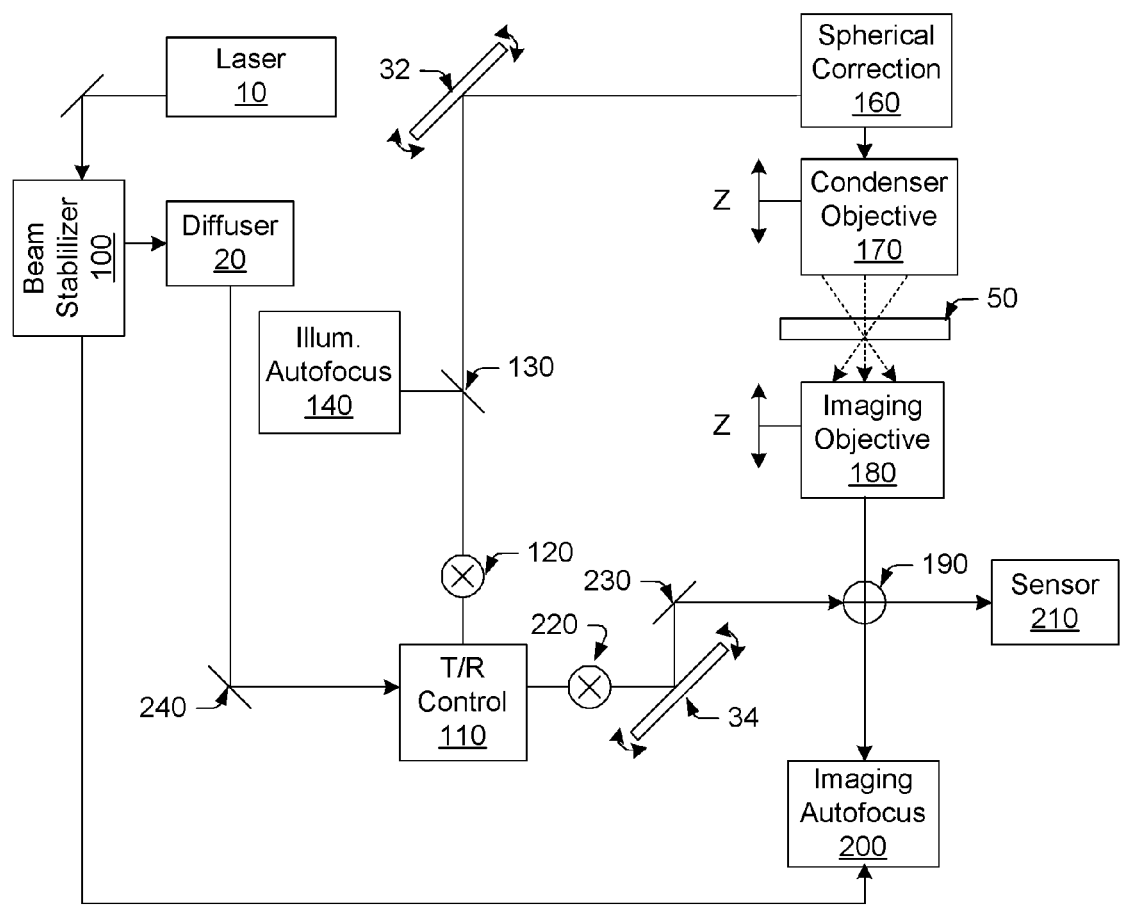
FIG. 4 is a block diagram of an inspection system, according to another embodiment of the invention.

The illumination system shown in FIG. 1 eliminates speckle in die-to-die inspection systems by ensuring that the illumination fields presented to two adjacent die are exactly the same. Various embodiments of a die-to-die inspection system comprising the illumination system are shown in FIGS. 3-4. Although the inspection systems are configured for operating in reflective and transmissive modes, one skilled in the art would understand how the illumination system described herein may be implemented in inspections systems comprising only one mode.

The inspection system embodiments shown in FIGS. 3-4 include many of the same components, which are denoted with like reference numerals. For instance, each of the inspection systems includes a laser light source 10 for generating coherent light. In some cases, a beam stabilizer 100 may be included within the inspection system for stabilizing the position and angle of the laser beam. The stabilized light from beam stabilizer 100 is directed to diffuser 20, as well as imaging auto-focus unit 190 (discussed below). The light exiting diffuser 20 is directed to reflective optical component 30, where it is reflected to a switch ("T/R control") 110 that determines whether the inspection system will operate in transmissive or reflective mode.

If transmissive mode is selected, the light passes through shutter 20 and impinges on beam splitter 130. A majority of the light from beam splitter 130 is reflected off optical component 150 to a spherical correction unit 160, which compensates for the spherical aberrations produced when the illumination light passes through the specimen 50. However, a small portion of the light is supplied to illumination auto-focus unit 140 for controlling the z-position of the illumination objective 170. This focuses the illumination light, and thus, the speckle field on the surface of the specimen.

Light transmitted through specimen 50 is collected by the imaging objective 180. An optical component 190 is included for supplying a portion of the imaging field to imaging auto-focus unit 200. The imaging auto-focus unit 200 focuses the image pattern by controlling the z-position of imaging objective 180, so that the surface of the specimen remains within the focus range of the imaging objective. Optical component 190 also supplies a portion of the collected light to sensor 210 for obtaining images of the specimen. As such, optical component 190 may include more than one optical component. For example, a field splitter may be arranged at the intermediate focal plane of the imaging objective 180 for supplying a portion of the imaging field to the imaging auto-focus unit 200. In addition, a beam splitter and lens may be included within optical component 190 for supplying a majority of the collected light to the sensor 210. The beam splitter may be arranged at a back focal plane of the lens, which is used to focus the collected light onto an imaging surface of the sensor 210.

If reflective mode is selected, the light from reflective optical component 30 passes through shutter 220 and impinges on the beam splitter within optical component 190. From here, light passes through imaging objective 180 to the surface of specimen 50. Light propagating from the surface of specimen 50 passes back through imaging objective 180 to optical component 190. As noted above, a field splitter may be included within optical component 190 for supplying a portion of the imaging field to imaging auto-focus unit 200. In addition, a beam splitter and lens may be included within optical component 190 for supplying a majority of the collected light to the sensor 210.

In FIG. 3, a single reflective optical component 30 is used for adjusting the angle at which the illumination light is directed to the surface of the specimen. This component is used regardless of whether the inspection system is operating in transmissive or reflective mode. However, the embodiment shown in FIG. 4 uses two separate reflective optical components (32, 34) for controlling the angle at which the illumination light is directed in transmissive and reflective modes. For example, reflective optical component 32 is included within the illumination path between shutter 120 and spherical correction unit 160 for controlling the illumination angle in transmissive mode. In addition, reflective optical component 34 is arranged in the illumination path between shutter 220 and optical component 190 for controlling the illumination angle in reflective mode. In some cases, one or more additional optical components 230/240 may be included within the inspection system for directing the light from diffuser 20 to switch 110 and from reflective optical component 34 to optical component 190.

Sensor 210 may include any appropriate detector known in the art, such as a charge coupled device (CCD) or time-delay integration (TDI) camera. In one embodiment, a TDI detector 210 is used to convert the optical images from imaging objective 180 into electronic signals. A TDI detector operates by moving the photo-electrons in a given image pixel synchronously with the stage movement in the x-direction. When the TDI detector completes one x-direction scan, the stage (60, FIG. 1) is stepped in the y-direction and the next x-direction scan is taken. The process continues until images are obtained over at least a portion of the specimen surface.

As noted above, speckle is reduced in conventional inspection systems by averaging a large number of images over the integration time of the detector. In one example, speckle may be reduced by a factor of 500 by averaging approximately 250,000 images over the integration time of the detector. Since a single speckled image has a 100% noise contrast, the noise reduction provided by the conventional averaging technique corresponds to a reduced noise contrast of about 0.002. Unfortunately, the amount of noise reduction provided by conventional systems may not be sufficient for inspecting newer technologies, which have smaller device dimensions, and thus, require higher signal-to-noise ratios to detect smaller defects.

Unlike conventional systems, the inspection systems described herein eliminate speckle noise by ensuring that the speckle illumination fields presented to two adjacent die are identical. As noted above, a coarse adjustment of the speckle field is provided by controlling the rotational rate of diffuser 20, so that an integral number of rotational periods occurs between identical features on the two die. Although not specifically shown in FIGS. 3-4, detectors 70 and 80 and controller 90 are included within the inspection systems described herein for that purpose. The operation of detectors 70 and 80 and controller 90 is described above in reference to FIG. 1.

In some cases, speckle noise may only be eliminated from the inspection images if the diffuser rotation is very closely matched to the movement of the stage. In one embodiment, the diffuser rotation may be closely matched to the movement of the stage if the number of pixels occurring within an integral (n) number of diffuser rotations is within one pixel of the die-to-die spacing (D) between identical features on two adjacent die. In order to achieve such tight tolerances, a fine adjustment is provided herein for making small adjustments to the speckle illumination field. Reflective optical components 30, 32, and 34 are included within the Fourier transform plane of the inspection systems for that purpose.

For example, the reflective optical component may be tilted in the x or y direction to adjust the angle at which the light is directed to the surface of the specimen. Since the reflective optical component lies within the Fourier transform plane of the illumination objective (e.g., lens 40, FIG. 1, and either objective 170 in FIGS. 3-4 when operating in transmissive mode or objective 180 in FIGS. 3-4 when operating in reflective mode), changes in the angle of the illumination light correspond to linear shifts in the position of the illumination light at the surface of the specimen. If the stage position measurement from detector 70 indicates that an x or y alignment error exists, the reflective optical component (e.g., 30, 32 or 34) in the active illumination path may be adjusted in the appropriate direction to make small adjustments to the speckle illumination field.

Figure 2A:
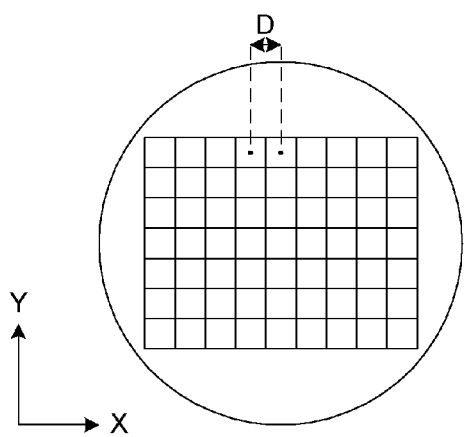
FIG. 2A is a top-side view of a wafer comprising a plurality of substantially identical die arranged in 7 rows and 9 columns.
Figure 2B:
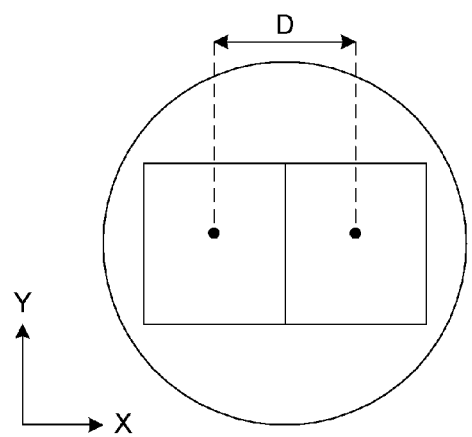
FIG. 2B is a top-side view of a mask comprising a plurality of substantially identical die arranged in 1 row and 2 columns.
Figure 5:
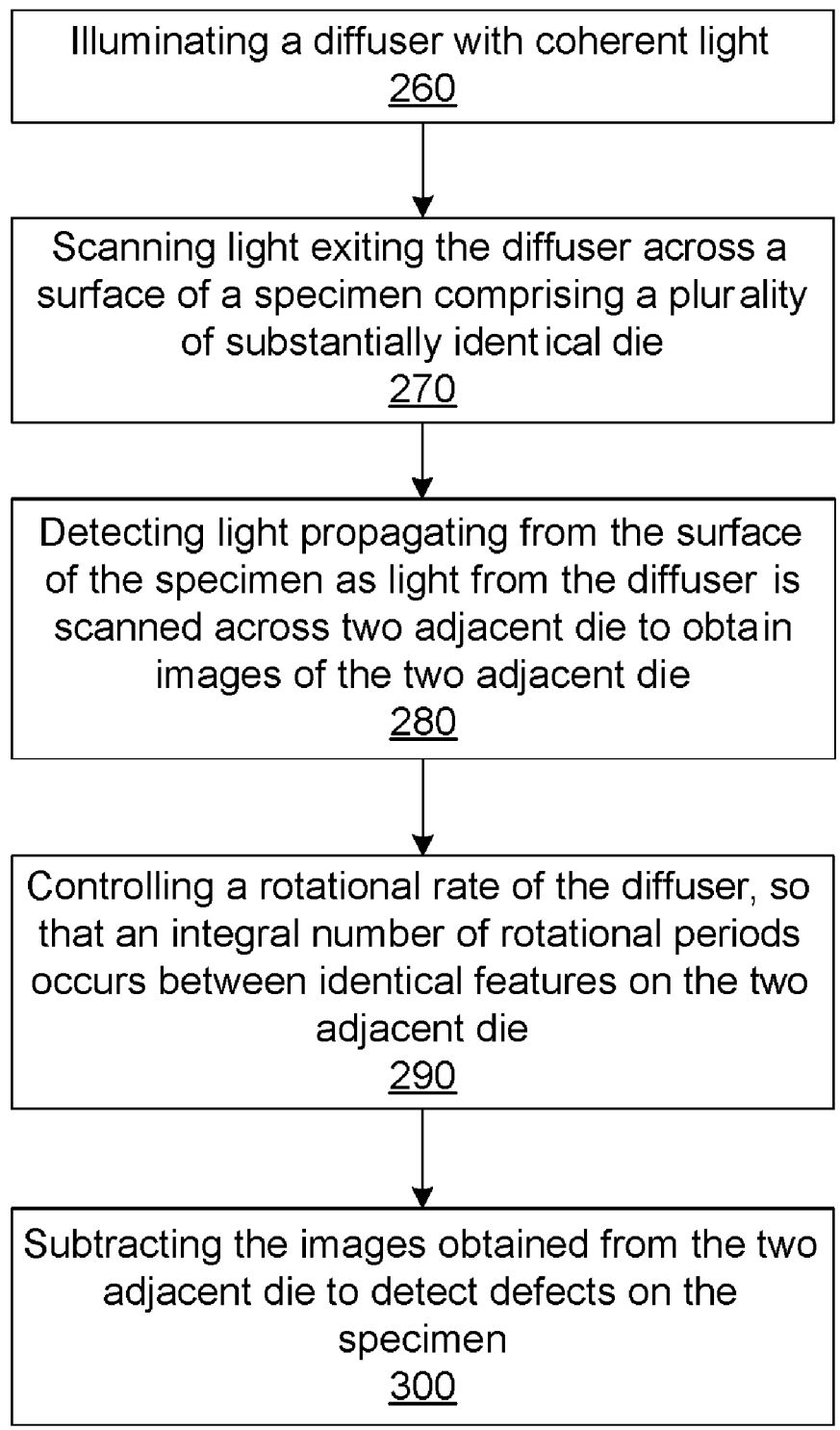
FIG. 5 is a flowchart diagram of a method for inspecting a specimen, according to one embodiment of the invention.

One embodiment of a method for inspecting a specimen is shown in FIG. 5. In some cases, the method may begin 260 by illuminating a diffuser with coherent light. The coherent light may originate from a laser light source, as shown in FIGS. 1 and 3-4. The light exiting the diffuser may be scanned 270 across a surface of a specimen comprising a plurality of substantially identical die. The specimen may comprise any wafer or mask, which includes an M×N array of substantially identical die. Examples of such specimens are shown in FIGS. 2A-2B. In step 280, the method detects light propagating from the surface of the specimen as light from the diffuser is scanned across two adjacent die to obtain images of the two adjacent die. Defects may be detected 300 when the images of the two adjacent die are subtracted from one another to remove the repeatable pattern of features included within each die. Unlike conventional methods, the inspection method described herein eliminates speckle noise in the inspection images by controlling 290 the rotational rate of the diffuser, so that an integral number of rotational periods occurs between identical features on the two adjacent die.

In one embodiment, the step of controlling 290 may include counting the number of times the coherent light passes through a reference mark on the diffuser (e.g., a scale) as the light from the diffuser is scanned between the identical features on the two adjacent die. The rotational rate of the diffuser may be increased if the number of times is less than the intended integral number of rotational periods, and decreased if the number of times is greater than the intended integral number of rotational periods. The rotational rate may be adjusted, in one embodiment, by modifying the power supplied to the diffuser motor.

If the number of times is not equivalent to the intended integral number of rotation periods after the rotational rate is adjusted, the method may further comprise adjusting an angle at which the light is directed to the surface of the specimen. The angle may be adjusted, in one embodiment, by changing the angle at which the light is reflected from optical component 30, 32, or 34. Since optical component 30, 32, and 34 are each arranged within the Fourier transform plane of the illumination objective (e.g., 40, 170, or 180), changes in the illumination angle correspond to linear shifts in the position of the illumination field provided to the specimen.

In another embodiment, the step of controlling 290 may include detecting a desired position on a specimen (e.g., a particular feature on a die), detecting a rotational position of the diffuser when the desired position on the specimen is detected, and controlling the diffuser rotational rate (R) so as to eliminate any difference between the rotational position of the diffuser and the desired position on the specimen. Such an embodiment is described in more detail above in reference to FIGS. 1 and 3-4.

For example, stage 60 (shown in FIG. 1) comprising the specimen 50 and the diffuser 20 providing the scattering may each have a reference mark imprinted thereon (e.g., a scale). A pair of detectors 70/80 may use these reference marks to determine the rotational position of the diffuser relative to that of the specimen, as the illumination light is scanned from one die to the next. One of the detectors 70 is used for detecting the spacing (D, expressed in number of pixels) between identical features on two adjacent die. The other detector is used for detecting the number of diffuser rotations (n, also expressed in pixels) that occur between the identical features. A controller 90 is used for comparing the number of pixels with measured values D and n, and for adjusting the diffuser rotational rate if any differences exist.

If the number of pixels, D, is not equal to an integer number of diffuser rotations, the diffuser rotational rate (R) may be increased or decreased by a proportional amount. For example, if the controller determines that the diffuser position measurement lags the stage position measurement by 0.4 pixels, the diffuser rotational rate may be increased to compensate for this difference. If the number of rotational periods (n) differs from the die-to-die spacing (D) by one or more pixels after the rotational rate is adjusted, the method may further comprise adjusting an angle at which the light is directed to the surface of the specimen. The angle may be adjusted, in one embodiment, by changing the angle at which the light is reflected from optical component 30, 32, or 34. Since optical component 30, 32, and 34 are each arranged within the Fourier transform plane of the illumination objective (e.g., 40, 170, or 180), changes in the illumination angle correspond to linear shifts in the position of the illumination field provided to the specimen.

In preferred embodiments, the various steps noted above for adjusting the rotational rate and adjusting the angle may be used to produce substantially identical noise patterns in each of the images by aligning a position of the diffuser with a desired position on the specimen. When the images of the two adjacent die are subtracted 300, the steps of adjusting the rotational rate and adjusting the angle increase the signal-to-noise ratio of the difference image by removing the substantially identical noise patterns produced in each of the images.

It will be appreciated to those skilled in the art having the benefit of this disclosure that this invention is believed to provide illumination systems, inspections systems and methods for inspecting specimens with reduced speckle noise. More specifically, the invention provides systems and methods for eliminating speckle noise from die-to-die inspection images. Further modifications and alternative embodiments of various aspects of the invention will be apparent to those skilled in the art in view of this description. It is intended, therefore, that the following claims be interpreted to embrace all such modifications and changes and, accordingly, the specification and drawings are to be regarded in an illustrative rather than a restrictive sense.

What is claimed is:

1. A system configured to provide illumination to a specimen under inspection, the system comprising:
   a diffuser coupled within an illumination path between a coherent light source and the specimen, wherein the diffuser comprises a variable rotational rate;
   a first detector configured to detect a desired position on the specimen;
   a second detector configured to detect a rotational position of the diffuser when the desired position on the specimen is detected; and
   a controller coupled to: (i) the first and second detectors for determining a difference between the rotational position of the diffuser and the desired position on the specimen, and (ii) the diffuser for adjusting the rotational rate of the diffuser to eliminate the difference.

2. The system as recited in claim 1, further comprising a reflective optical component arranged within the illumination path for directing light exiting the diffuser onto a surface of the specimen.

3. The system as recited in claim 2, further comprising a lens arranged within the illumination path for focusing the light, which is directed onto the surface of the specimen.

4. The system as recited in claim 3, further comprising an auto-focus unit coupled within the illumination path for adjusting a position of the lens to maintain the surface of the specimen within a focus region of the lens.

5. The system as recited in claim 3, wherein the controller is coupled to the reflective optical component for adjusting an angle at which the light is directed onto the surface of the specimen, and wherein the lens is configured to convert the angular adjustment into a linear shift in position of the light directed to the surface.

6. The system as recited in claim 3, further comprising a stage upon which the specimen is mounted, wherein movement of the stage causes the focused light to be scanned across two adjacent die on the specimen.

7. The system as recited in claim 6, wherein the controller is configured to adjust the rotational rate of the diffuser, so that an integral number of rotational periods occurs between identical features on the two adjacent die.

8. The system as recited in claim 6, wherein the stage and the diffuser each have a reference mark that enables the first and second detectors to detect the desired position and the rotational position, respectively.

9. A system configured to inspect a specimen, comprising:
an illumination subsystem comprising a rotating diffuser arranged within an illumination path between a coherent light source and the specimen;
a detection subsystem comprising a first detector, which is coupled for detecting a desired position on the specimen, and a second detector, which is coupled for detecting a rotational position of the diffuser when the desired position is detected; and
a control subsystem coupled to: (i) the first and second detectors for determining a difference between the rotational position of the diffuser and the desired position on the specimen, and (ii) the diffuser for adjusting a rotational rate of the diffuser to eliminate the difference.

10. The system as recited in claim 9, wherein the illumination subsystem further comprises:
a reflective optical component arranged within the illumination path for directing light exiting the diffuser across a surface of the specimen;
a lens arranged within the illumination path for focusing the light, which is directed onto the surface of the specimen; and
a stage upon which the specimen is mounted, wherein movement of the stage causes the focused light to be scanned across two adjacent die on the specimen.

11. The system as recited in claim 10, wherein the control subsystem is coupled to the reflective optical component for adjusting an angle at which the light is directed onto the surface of the specimen, and wherein the lens is configured to convert angular adjustments of the reflective optical component into linear shifts in the position of the light directed onto the surface.

12. The system as recited in claim 11, wherein the detection subsystem comprises a third detector, which is coupled for receiving light propagating from the surface of the specimen and configured for generating images of the two adjacent die in response thereto, wherein the images are used for detecting defects on the specimen.

13. The system as recited in claim 12, wherein the control subsystem causes substantially identical speckle noise patterns to be produced in the images of the two adjacent die by:
adjusting the rotational rate of the diffuser, so that an integral number of rotational periods occurs between identical features on the two adjacent die; and
adjusting the angle at which the light is directed onto the surface of the specimen, such that the difference between the rotational position of the diffuser and the desired position on the specimen is substantially zero.

14. The system as recited in claim 13, wherein a substantially zero difference is equivalent to about one image pixel, as measured by the first and second detectors.

15. A method for inspecting a specimen comprising a plurality of die having substantially identical features, the method comprising:
illuminating a diffuser with coherent light;
scanning light exiting the diffuser across a surface of the specimen;
detecting light propagating from the surface of the specimen as light from the diffuser is scanned across two adjacent die to obtain images of the two adjacent die;
controlling a rotational rate of the diffuser, so that an integral number of rotational periods occurs between identical features on the two adjacent die; and
subtracting the images obtained from the two adjacent die to detect defects on the specimen.

16. The method as recited in claim 15, wherein the step of controlling comprises:
counting the number of times the coherent light passes through a reference mark on the diffuser as the light from the diffuser is scanned between the identical features on the two adjacent die; and
adjusting the rotational rate of the diffuser, wherein the rotational rate is increased if the number of times is substantially less than the integral number, and decreased if the number of times is substantially greater than the integral number.

17. The method as recited in claim 16, wherein if the number of times is not equivalent to the integral number after the steps of counting and adjusting, the method further comprises adjusting an angle at which the light is directed onto the surface of the specimen.

18. The method as recited in claim 17, wherein the angle can be adjusted in one or more directions to produce a linear shift in position of the light directed to the surface of the specimen.

19. The method as recited in claim 17, wherein the steps of adjusting the rotational rate and adjusting the angle are configured to produce substantially identical noise patterns in each of the images by aligning a position of the diffuser with a desired position on the specimen.

20. The method as recited in claim 19, wherein the step of subtracting reduces noise in the images obtained from the two adjacent die by removing the substantially identical noise patterns produced in each of the images.

* * * * *